United States Patent [19]

Washer

[11] 4,371,731
[45] Feb. 1, 1983

[54] ALKYLATION PROCESS

[75] Inventor: Stone P. Washer, Bartlesville, Okla.

[73] Assignee: Phillips Petroleum Company, Bartlesville, Okla.

[21] Appl. No.: 299,427

[22] Filed: Sep. 4, 1981

[51] Int. Cl.³ ............................................... C07C 2/56
[52] U.S. Cl. .................................... 585/716; 585/723
[58] Field of Search ........................ 585/710, 716, 723

[56] References Cited

U.S. PATENT DOCUMENTS

| | | | |
|---|---|---|---|
| 2,375,867 | 5/1945 | Newman | 585/251 |
| 2,394,929 | 2/1946 | Matuszak | 585/717 |
| 2,417,875 | 3/1947 | Leonard | 585/704 |
| 2,507,764 | 5/1950 | Carnell | 585/331 |
| 2,544,559 | 3/1951 | Matuszak | 208/298 |
| 3,204,010 | 8/1965 | Van Pool | 585/712 |
| 3,204,011 | 8/1965 | Hettick et al. | 585/703 |
| 3,780,131 | 12/1973 | Sobel | 585/716 |

*Primary Examiner*—Curtis R. Davis

[57] ABSTRACT

A combination process for production of HF alkylate motor fuel and HF alkylate solvent wherein the alkyl fluoride impurities present in the produced motor fuel are removed therefrom by treatment with a relatively clean HF stream (emulsion) containing the produced HF alkylate solvent. Makeup, relatively clean, HF catalyst for the motor fuel alkylation is secured from the solvent HF alkylate alkylation system.

The invention produces motor fuel alkylate substantially free of organic fluoride contaminates as well as substantially organic fluoride-free isoparaffin solvent alkylate, using only one HF rerun column.

9 Claims, 1 Drawing Figure

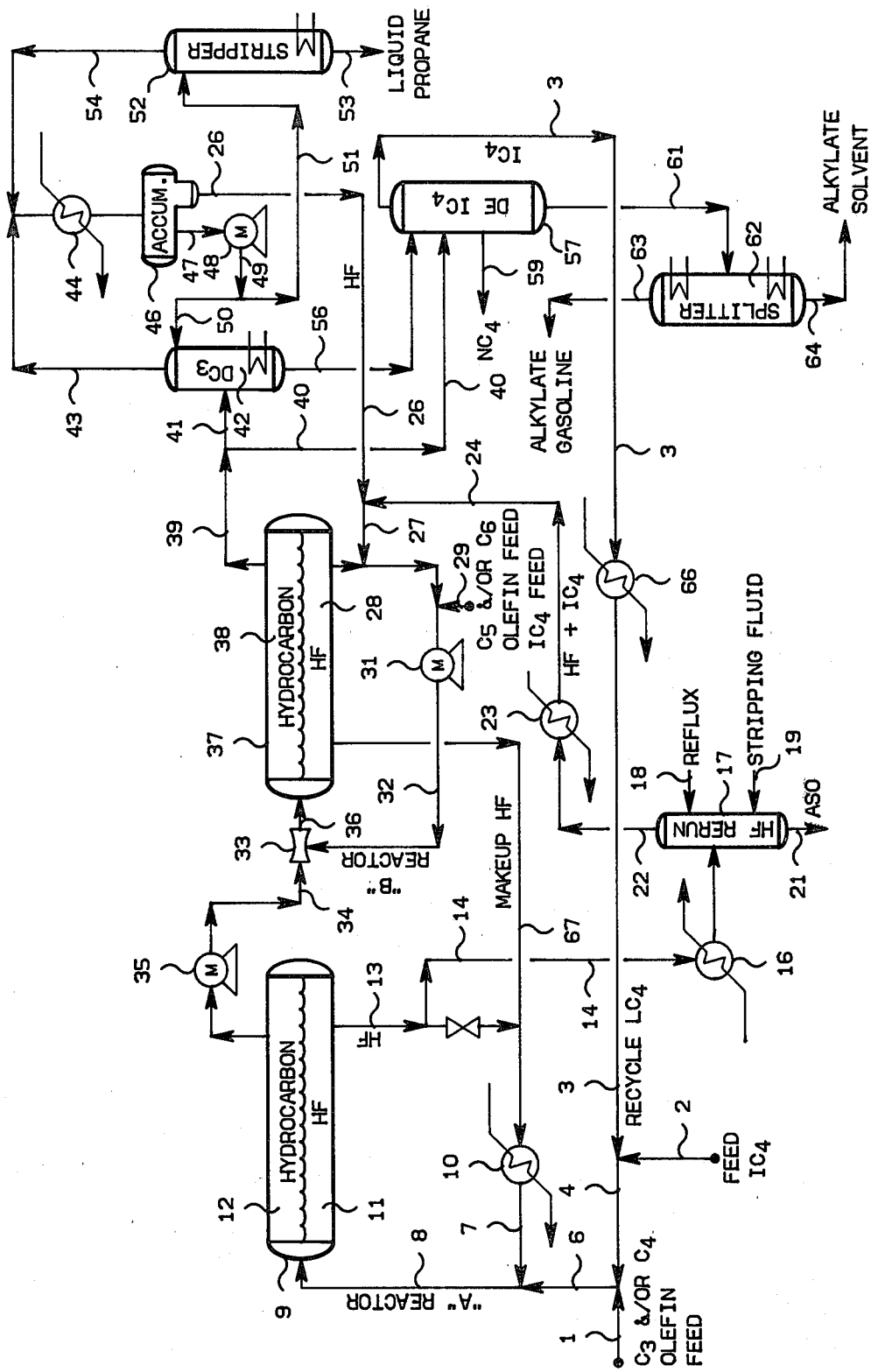

ALKYLATION PROCESS

This invention relates to alkylation of hydrocarbons. In another aspect, this invention relates to processes for treating organic compounds with hydrogen fluoride (HF). In another aspect, this invention relates to a combination process for the production of alkylate motor fuel and alkylate solvent. In another aspect, this invention relates to an improved process for the production of HF alkylate motor fuel and HF alkylate solvent wherein the alkyl fluoride impurities present in the produced motor fuel are removed by treatment with a relatively clean HF stream containing the produced HF alkylate solvent.

In the manufacture of hydrocarbons by processes wherein fluorine-containing catalysts, such as hydrogen fluoride, are used small proportions of organic fluorine-containing by-products are formed. Such processes can invoke such reactions as isomerization, polymerization, alkylation and disproportionation of relatively low boiling hydrocarbons. Such processes are well known. One class of by-products which is formed and which must be removed from the products comprises organic alkyl fluorides.

In those processes wherein low boiling hydrocarbons, such as propane and lighter, are formed, the presence of alkyl fluoride is not particularly objectionable for some end uses of the hydrocarbons. However, for other end uses, it is essential that the hydrocarbon be substantially free of fluorine compounds, such as the alkyl fluorides.

The present invention is a combination process for the production of alkylate motor fuel and alkylate solvent wherein alkyl fluoride impurities present in the produced motor fuel are removed therefrom.

Accordingly, an object of this invention is to provide an improved alkylation process.

Another object of this invention is to provide a combination alkylation process for the production of motor fuel alkylate and solvent alkylate.

A further object of this invention is to provide a process for removing fluoride compounds from alkylation products.

A further object of this invention is to provide a combination process for the manufacture of solvent alkylate without detriment to gasoline alkylate quality or quantity.

Other objects, aspects, as well as the several advantages of the invention will be clear to one skilled in the art upon a study of the disclosure including the description of the drawing and the appended claims.

This invention is a combination process for the production of alkylate motor fuel and alkylate solvent in separate alkylate zones using different olefins wherein the alkyl fluoride impurities present in the produced motor fuel are removed therefrom by treatment with a relatively clean HF stream containing the produced HF alkylate solvent. The motor fuel alkylation unit uses a conventional liquid HF catalyst while the solvent HF alkylate system uses a relatively pure liquid HF catalyst containing isoparaffins, such as isobutane, absorbed from the motor fuel alkylation reactor effluent hydrocarbon stream, plus isobutane from the rerun overhead, and isobutane injected for reaction with $C_5$ and $C_6$ olefins. This latter HF catalyst containing stream is admixed with very pure HF liquid catalyst recovered from a separation system following alkylation and the recycled solvent alkylate system HF liquid catalyst. The invention produces motor fuel alkylate substantially free of organic fluoride contaminants as well as substantially organic fluoride-free isoparaffin solvent alkylate using only one HF catalyst rerun unit.

The sole FIGURE is a schematic flow diagram illustrating a specific embodiment of the invention as applied to a combination process for production of HF alkylate motor fuel and HF alkylate solvent wherein the alkyl fluoride impurities present in the produced motor fuel are removed therefrom. The process of the invention will now be described with reference to the drawing. It is to be understood that numerous items of equipment, such as pumps, valves, and the like, have been omitted from the drawing so as to simplify the description of the invention. Those skilled in the art will realize that such conventional equipment can be employed as desired.

DESCRIPTION OF THE DRAWING

Olefin feed, such as propylene and/or butylenes, is charged to the system via conduit 1. Feed isoparaffin, such as isobutane, is charged via conduit 2 along with recycle isobutane 3 (source is described below) and the isobutane feed and isobutane recycle pass via conduit 4 into admixture with the olefin feed from conduit 1. The total admixture is passed via 6 having HF alkylation catalyst 7 added thereto, and the admixture enters alkylation reactor "A", designated 8, wherein part of isobutane is alkylated by the olefins to produce gasoline quality alkylate. The effluent liquid emulsion from reactor 8 passes to liquid phase separator 9 wherein a lower liquid HF catalyst phase 11 and an upper liquid hydrocarbon phase 12 (excess isobutane, propane, normal butane, gasoline alkylate, organic fluorides, and dissolved HF) are formed.

The conditions obtaining in the motor fuel alkylate alkylation zone (reactor "A") are conventional for temperatures, pressures, and hydrocarbon ratios. A typical operation will include a temperature in the range of about 40° F. to about 120° F., pressures to maintain liquid phases, an isoparaffin to olefin volume ratio of about 4 to 1 to about 20 to 1, and an HF to total hydrocarbon volume ratio of about 0.5 to 1 to about 10 to 1.

System HF catalyst is removed from vessel 9 via conduit 13 and, in major portion, is passed through indirect cooler 10 and recycled by 7 to "A" reactor 8.

A portion of the system acid is passed from 13 via conduit 14 and vaporizer 16 to HF catalyst rerun unit 17 into which, preferably, liquid isobutane (e.g., from conduit 3) is charged as reflux 18, and vaporous isobutane 19 (e.g., vaporized isobutane from 3) is used as stripping vapor. Acid soluble oils are removed via conduit 21.

Vaporous isobutane and regenerated HF are passed via 22, indirect condenser 23, and conduit 24 to conduit 27, into which conduit 27 is added HF liquid 26, described hereinbelow. The admixture of HF liquid 26 and HF and isobutane from conduit 26 present in conduit 27, along with liquid HF and absorbed isoparaffins from 28, described below, are contacted with pentenes and/or hexenes 29 along with feed isoparaffin, e.g., isobutane, also charged via 29, and the emulsion from pump 31 is charged to "B" reactor, designated conduit 32.

In reactor "B", the added pentenes and/or hexenes react with the isobutane to produce solvent alkylate and this emulsion passes via 32 to eductor mixer 33 into which stream 34 is pumped by pump 35. Within eductor-mixer 33, the relatively clean HF in stream 32 in the presence of isobutane in the admixture reacts out the organic fluorides entering in stream 34 (and even in stream 32) to produce additional alkylate and release additional HF.

The alkylation conditions obtaining in reactor "B" are conventional and can be substantially as set forth for reactor "A", above.

The mass from 33 is passed via 36 to liquid phase separator 37 wherein an upper liquid hydrocarbon phase 38 and a lower HF liquid phase 28 are formed. This liquid HF 28 is added to the HF liquid from stream 27, above-described. Hydrocarbon phase 38 (propane, unreacted isobutane, normal butane, gasoline alkylate (from reactor "A") and solvent alkylate, along with dissolved HF) is passed via 39 to conventional fractionation.

A portion of stream 39 is passed via 41 to depropanizing unit 42 in an amount to remove net propane from the system. Overhead vapor 43 from depropanizer 42 is condensed at 44, along with stream 54, described below, and passed to accumulator 46. Liquid hydrocarbon phase from 46 is passed via 47, pump 48, and conduit 49 wherefrom liquid reflux 50 is passed to depropanizer 42, and yield hydrocarbon is passed via 51 to stripper 52. Liquid propane yield is removed at 53, for further treatment, as desired. Overhead vapor 54, comprising HF and propane, is condensed in exchanger 44, above-described.

The other portion of hydrocarbon 39 is passed by 40 to deisobutanizer 57. Overhead vapor isobutane is removed via 3, condensed at 66, and recycled to HF alkylation reactor "A", above-described. Also charged to deisobutanizer 57 is the depropanizer bottom 56, which is rich in isobutane and contains normal butane, gasoline alkylate, and solvent alkylate. Normal butane (vapor) is recovered at 59 for further processing. Bottoms 61 from deisobutanizer 57 is charged to alkylate splitter 62 which yields gasoline alkylate at 63 and solvent alkylate at 64.

Makeup catalyst for reactor "A" is obtained from the HF liquid phase 28 via conduit 67.

The temperatures and pressures of the distillation steps will be substantially the same when the process of the invention is practiced as those of the prior art process.

The operation of a typical system, such as shown in the drawing, is reflected in the material balance of the following tabulation wherein the materials of the numbered columns represent the materials at the location of corresponding numbers on the drawing.

| Typical Operation (Calculated) | |
|---|---|
| A. Operating Conditions: | |
| (8) Reactor "A": | |
| Temperature, °F., | 90 |
| Pressure, psig, | 140 |
| IC$_4$/Olefin Liquid Volume Ratio, feed about 12:1 | |
| HF/Total Hydrocarbon, Vol. Ratio, feed about 4:1 | |
| Reaction Time, seconds, | 30 |
| (9) Phase Separator: | |
| Temperature, °F., | 94 |
| Pressure, psig, | 139 |
| (32) Reactor "B": | |
| Temperature, °F., | 94 |
| Pressure, psig, | 145 |
| IC$_4$/Olefin Liquid Volume Ratio, feed about 11:1 | |
| HF/Total Hydrocarbon, Vol. Ratio, feed about 10:1 | |
| Reaction Time, seconds | 20 |
| (33) and (36) Recontact Zone: | |
| Temperature, °F., | 95 |
| Pressure, psig., | 145 |
| HF/Total Hydrocarbon, Vol. Ratio, | 1:1 |
| Contact Time, seconds | 10 |
| (42) Depropanizer: | |
| Pressure, psig., | 275 |
| Temperatures: | |
| Top, °F., | 128 |
| Bottom, °F., | 230 |
| (52) Stripper: | |
| Pressure, psig., | 280 |
| Temperatures: | |
| Top, °F., | 129 |
| Bottom, °F., | 130 |
| (57) Deisobutanizer: | |
| Pressure, psig., | 125 |
| Temperatures: | |
| Top, °F., | 147 |
| Bottom, °F., | 350 |
| Note that depropanizer 42 and deisobutanizer 57 can be a single column. | |
| (62) Alkylate Splitter: | |
| Pressure, psig., | 20 |
| Temperatures: | |
| Top, °F., | 140 |
| Bottom, °F., | 425 |
| (17) HF Rerun Unit: | |
| Pressure, psig., | 100 |
| Temperatures: | |
| Top, °F., | 280 |
| Bottom, °F., | 325 |

| B. Flow Rates: | | Barrels/Hour |
|---|---|---|
| (1) FCC C$_3$'s and C$_4$'s (about 60% olefin) | | 480 |
| (2) Isobutane Feed, | | 313 |
| (3) Recycle Isobutane, (88 LV %) | | 4,030 |
| (4) HF Liquid, | | 18,800 |
| Composition, | L.V. % | |
| HF, | 90.0 | |
| H$_2$O, | 1.5 | |
| ASO, | 3.5 | |
| IC$_4$, | 3.0 | |
| Other H/C, | 2.0 | |
| (34) Hydrocarbon Phase, | | 4,700 |
| [200 ppm (wt.) Organic Fluorides] | | |
| (29) Pentenes & hexenes 20 BPH, iC$_4$ 20 BPH, | | 40 |
| (32) Reactor "B" Emulsion, | | |
| Composition, | L.V. % | |
| Hydrocarbon, | 6.0 | |
| HF, | 92 | |
| ASO, | 2.0 | |
| (41) Feed to Depropanizer (42), | | 1,020 |
| (53) Propane Yield, | | 51 |
| (40) Feed to Deisobutanizer (57), | | 982 |
| (56) Feed to Deisobutanizer (57), | | 3,680 |
| (3) Recycle Isobutane (as Liquid), (88 L.V. %) | | 4,030 |
| (59) Normal Butane (as Liquid), | | 22 |
| (61) Feed to Splitter (62), | | 580 |
| (64) Solvent Alkylate, (27 B/H of "A" and 34 B/H of "B") | | 61 |
| Boiling Range: | | |
| Initial, °F., 300 | | |
| End Point, °F., 550 | | |
| Organic Fluorides, ppm 25 | | |
| HF, ppm 5 | | |
| (63) Motor Fuel Alkylate | | 519 |
| Boiling Range: | | |
| Initial, °F., 80 | | |
| End Point, °F., 338 | | |
| RON clear, 93 | | |
| Organic Fluorides, ppm, 25 | | |

| Typical Operation (Calculated) | |
| --- | --- |
| HF, ppm, | 5 |

L.V. = Liquid Volume
ppm by wt.

The material balance shows that the fluorides are reduced from 200 ppm to 25 ppm.

The main point of this invention is to manufacture solvent alkylate without detriment to gasoline alkylate quantity or quality by taking advantage of the isobutane within the HF acid circulating between settler 37 and the eductor-mixer 33, the major portion of the isobutane being that isobutane absorbed in HF from phase 28.

I claim:

1. A combination process for production of motor fuel alkylate and solvent alkylate without detriment to motor fuel alkylate quality or quantity which comprises
   (a) contacting an isoparaffin with an olefin comprising $C_3$ and/or $C_4$ olefins in the presence of an HF acid catalyst in a first alkylation zone under alkylation conditions which produce a motor fuel alkylate,
   (b) separating the effluent product of (a) into an HF acid phase containing absorbed isoparaffin and a hydrocarbon phase comprising unreacted isoparaffin, light hydrocarbons, including normal paraffins, motor fuel alkylate, organic fluorides and HF,
   (c) regenerating at least a portion of said HF acid phase in (b) in the presence of an isoparaffin under conditions which produce regenerated HF acid containing isoparaffins,
   (d) contacting at least a portion of said regenerated HF acid containing isoparaffin with an olefin comprising $C_5$ and/or $C_6$ olefins in a second alkylation zone under alkylation conditions which produce solvent alkylate,
   (e) mixing said solvent alkylate with said hydrocarbon phase in (b) in a mixing zone under conditions which produce an effluent reduced in said organic fluorides and containing additional alkylate,
   (f) separating said effluent in (e) into an HF acid phase and a hydrocarbon phase, and
   (g) subjecting said hydrocarbon phase in (f) to fractionation to separately recover alkylate products, isoparaffin, normal paraffins, and HF acid.

2. A process according to claim 1 wherein at least a portion of the HF acid catalyst in (a) is said HF acid phase separated in (f).

3. A process according to claim 1 wherein at least a portion of said HF acid in (d) comprises HF acid recovered in (g).

4. A process according to claim 1 wherein said isoparaffin in (a) and (c) is isobutane.

5. A process according to claim 1 wherein said isoparaffin recovered in (g) is recycled as at least part of said isoparaffin in (a).

6. A process according to claim 1 wherein said HF acid regenerated in (c) is contacted with isobutane under conditions which form regenerated HF acid containing isobutane and acid soluble oil (ASO) for discard.

7. A process according to claim 6 wherein said regenerated HF acid, containing isobutane, is combined with HF acid recovered in (f) and (g) and using the mixture thus-formed as the source of HF acid in (d) for contact with said olefins.

8. A process according to claim 1 wherein mixing in (e) is carried out in an eductor-mixer.

9. A process according to claim 1 wherein said isoparaffin is isobutane and further wherein at least a portion of the HF acid catalyst in (a) is said HF acid phase separated in (f) and wherein at least a portion of said HF acid in (d) comprises HF acid recovered in (g) and wherein said regenerated HF acid containing isobutane contained in (c) is combined with HF acid recovered in (f) and (g) and used as the source of HF acid in (d) for contact with said olefins.

* * * * *